United States Patent
Zhang et al.

(10) Patent No.: US 10,311,744 B2
(45) Date of Patent: Jun. 4, 2019

(54) AUTODIDACTIC COGNITIVE TRAINING DEVICE AND METHOD THEREOF

(71) Applicants: Agency for Science, Technology and Research, Singapore (SG); National University of Singapore, Singapore (SG)

(72) Inventors: Hai Hong Zhang, Singapore (SG); Cuntai Guan, Singapore (SG); Ranga Krishnan, Singapore (SG); Tih Shih Lee, Singapore (SG); Zheng Yang Chin, Singapore (SG); Chuan Chu Wang, Singapore (SG)

(73) Assignees: Agency for Science, Technology and Research, Singapore (SG); National University of Singapore, Singapore (SG)

( * ) Notice: Subject to any disclaimer, the term of this patent is extended or adjusted under 35 U.S.C. 154(b) by 0 days.

(21) Appl. No.: 14/423,614

(22) PCT Filed: Aug. 22, 2013

(86) PCT No.: PCT/SG2013/000363
§ 371 (c)(1),
(2) Date: Feb. 24, 2015

(87) PCT Pub. No.: WO2014/031083
PCT Pub. Date: Feb. 27, 2014

(65) Prior Publication Data
US 2015/0187227 A1    Jul. 2, 2015

(30) Foreign Application Priority Data
Aug. 24, 2012    (SG) .............................. 2012063012

(51) Int. Cl.
*G09B 19/00* (2006.01)
*A61B 5/00* (2006.01)
(Continued)

(52) U.S. Cl.
CPC ............ *G09B 19/00* (2013.01); *A61B 5/0077* (2013.01); *A61B 5/0476* (2013.01); *A61B 5/162* (2013.01);
(Continued)

(58) Field of Classification Search
CPC ....... A61B 5/0006; A61B 5/0476; A61B 5/16; A61B 5/4088; A61B 5/72; A61B 5/7271
(Continued)

(56) References Cited

U.S. PATENT DOCUMENTS 5,295,491 A * 3/1994 Gevins ................. A61B 5/0484
600/544
5,447,166 A * 9/1995 Gevins ................. A61B 5/0484
128/925
(Continued)

FOREIGN PATENT DOCUMENTS

WO    WO-2014/031083    2/2014

OTHER PUBLICATIONS

"International Application No. PCT/SG2013/000363, International Search Report and Written Opinion dated Oct. 18, 2013", (Oct. 18, 2013), 15 pgs.

*Primary Examiner* — Robert J Utama
(74) *Attorney, Agent, or Firm* — Schwegman Lundberg & Woessner, P.A.

(57) ABSTRACT

A cognitive training method has a step of obtaining sensor data of a subject during a memory exercise which in turn determines whether the sensor data includes predetermined information indicative of cognitive functions used for remembering. The step of advancing the memory exercise is
(Continued)

carried out when it is determined that the sensor data includes predetermined information indicative of cognitive functions used for remembering. The step of calculating an objective cognitive assessment of the subject is carried out when the memory exercise is completed and cognitive training is measured at least partially in response to the advancing of the memory exercise. The fact that an objective cognitive assessment is calculated provides a method of using an autodidactic cognitive training device.

25 Claims, 5 Drawing Sheets

(51) Int. Cl.
*A61B 5/16* (2006.01)
*A61B 5/0476* (2006.01)
*G02B 6/12* (2006.01)
*G02F 1/01* (2006.01)
*G02F 1/025* (2006.01)
*G02F 1/225* (2006.01)
*G09B 5/08* (2006.01)
*G09B 5/06* (2006.01)

(52) U.S. Cl.
CPC .............. *A61B 5/4088* (2013.01); *A61B 5/72* (2013.01); *G02B 6/12033* (2013.01); *G02F 1/0147* (2013.01); *G02F 1/025* (2013.01); *G02F 1/225* (2013.01); *A61B 5/742* (2013.01); *A61B 5/7475* (2013.01); *G02F 2203/585* (2013.01); *G09B 5/06* (2013.01); *G09B 5/065* (2013.01); *G09B 5/08* (2013.01)

(58) Field of Classification Search
USPC ......................................................... 434/236
See application file for complete search history.

(56) References Cited

U.S. PATENT DOCUMENTS

| | | | | |
|---|---|---|---|---|
| 5,724,987 A * | 3/1998 | Gevins | ................. | A61B 5/0484 434/258 |
| 6,097,981 A * | 8/2000 | Freer | .................... | A61B 5/0482 600/544 |
| 6,626,676 B2 * | 9/2003 | Freer | .................... | A61B 5/0482 434/236 |
| 8,989,835 B2 * | 3/2015 | Badower | ................. | A61B 5/00 600/383 |
| 2002/0192624 A1 * | 12/2002 | Darby | ...................... | A61B 5/16 434/236 |
| 2004/0002043 A1 * | 1/2004 | Dowrick | ................... | G09B 5/06 434/178 |
| 2006/0121427 A1 * | 6/2006 | Skoglund | ................ | G09B 7/00 434/236 |
| 2007/0293735 A1 * | 12/2007 | Chan | ........................ | A61B 5/16 600/300 |
| 2008/0171584 A1 * | 7/2008 | Roberts | ................... | A63F 13/10 463/9 |
| 2008/0275358 A1 * | 11/2008 | Freer | ....................... | G09B 7/02 600/544 |
| 2011/0238685 A1 * | 9/2011 | Garcia Molina | .... | A61B 5/0476 707/769 |
| 2012/0108997 A1 * | 5/2012 | Guan | ................. | A61B 5/04014 600/545 |
| 2012/0130266 A1 * | 5/2012 | Mathan | ............... | A61B 5/4833 600/544 |
| 2015/0126899 A1 * | 5/2015 | Ghajar | .................... | G09B 5/02 600/558 |
| 2016/0262680 A1 * | 9/2016 | Martucci | ................ | A61B 5/162 |

* cited by examiner

AUTODIDACTIC COGNITIVE TRAINING DEVICE AND METHOD THEREOF

PRIORITY CLAIM TO RELATED APPLICATIONS

This application is a U.S. National Stage application filed under 35 U.S.C. § 371 from International Application Serial No. PCT/SG2013/000363, which was filed Aug. 22, 2013, and published as WO2014/031083 on Feb. 27, 2014, and which claims priority to Singapore Application No. 201206301-2, filed Aug. 24, 2012, which applications and publication are incorporated by reference as if reproduced herein and made a part hereof in their entirety, and the benefit of priority of each of which is claimed herein.

FIELD OF INVENTION

The invention relates generally to an autodidactic cognitive training device and method thereof.

BACKGROUND

Memory loss is a common neurodegenerative condition that comes with aging. It is especially so for patients diagnosed with dementia, which is a set of signs and symptoms affecting the cognitive functions of memory. One such example of, dementia is Alzheimer's diseases. Approved drugs are used on patients with Alzheimer's diseases but they do not cure or prevent the symptoms. Therefore, alternative interventions are called for to treat the memory loss of the patients.

Trans-cranial direct current stimulation (tDCS) is one such alternative intervention. It is a neuromodulatory method that delivers low-intensity, direct current to cortical areas facilitating or inhibiting spontaneous neuronal activity. However, since tDCS elicits after-effects lasting for up to an hour, it may in some instances cause unnecessary side-effects to the cognitive functions of the subject.

With the existing techniques and tools, it is difficult to provide a personalized memory training system that meets the needs of the subject. Each subject has a different degree of affected memory functions, i.e., a patient of dementia may exhibit two or more dementing processes at the same time. It is also possible for a subject to advance in the dementing processes at a different rate, making it difficult to provide an objective assessment of the cognitive functions of memory. An objective cognitive assessment will be helpful to provide a personalized training program to aid in the training of the cognitive functions of a subject.

A need therefore exists to provide an objective cognitive assessment which can be used to provide a personalized memory training program.

SUMMARY

According to a first aspect, there is provided a method for cognitive training, the method comprising obtaining sensor data of a subject during a memory exercise; determining whether the sensor data includes predetermined information indicative of cognitive functions used for remembering; advancing the memory exercise when it is determined that the sensor data includes predetermined information indicative of cognitive functions used for remembering; and calculating an objective cognitive assessment of the subject in response to completion of the memory exercise, wherein cognitive training is measured at least partially in response to the advancing of the memory exercise.

According to a second aspect, there is provided an autodidactic cognitive training device comprising an input device for receiving the sensor data of a subject during a memory exercise; a cognitive function evaluator adapted to receive the sensor data from the input device and determine whether the sensor data includes predetermined information indicative of cognitive functions used for remembering; an exercise device adapted to advance the memory exercise when it is determined that the sensor data includes the predetermined information indicative of cognitive functions used for remembering, the exercise device comprising a calculating device adapted to calculate an objective cognitive assessment of the subject in response to completion of the memory exercise.

According to a third aspect, there is provided a system comprising two or more devices according to the second aspect as described above wherein the receiver is further operable to receive the objective cognitive assessment of two or more subjects corresponding to the two or more devices and the server operable to correlate the two or more subjects with their respective objective cognitive assessments.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

Some portions of the description which follows are explicitly or implicitly presented in terms of algorithms and functional or symbolic representations of operations on data within a computer memory. These algorithmic descriptions and functional or symbolic representations are the means used by those skilled in the data processing arts to convey most effectively the substance of their work to others skilled in the art. An algorithm is here, and generally, conceived to be a self-consistent sequence of steps leading to a desired result. The steps are those requiring physical manipulations of physical quantities, such as electrical, magnetic or optical signals capable of being stored, transferred, combined, compared, and otherwise manipulated.

Unless specifically stated otherwise, and as apparent from the following, it will be appreciated that throughout the present specification, discussions utilizing terms such as "scanning", "calculating", "determining", "replacing", "generating", "initializing", "outputting", or the like, refer to the action and processes of a computer system, or similar electronic device, that manipulates and transforms data represented as physical quantities within the computer system into other data similarly represented as physical quantities within the computer system or other information storage, transmission or display devices.

The present specification also discloses apparatus for performing the operations of the methods. Such apparatus may be specially constructed for the required purposes, or may comprise a general purpose computer or other device selectively activated or reconfigured by a computer program stored in the computer. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate. The structure of a conventional general purpose computer will appear from the description below.

In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer effectively results in an apparatus that implements the steps of the preferred method.

The invention may also be implemented as hardware modules. More particular, in the hardware sense, a module is a functional hardware unit designed for use with other components or modules. For example, a module may, be implemented using discrete electronic components, or it can form a portion of an entire electronic circuit such as an Application Specific Integrated Circuit (ASIC). Numerous other possibilities exist. Those skilled in the art will appreciate that the system can also be implemented as a combination of hardware and software modules.

Figure 1:
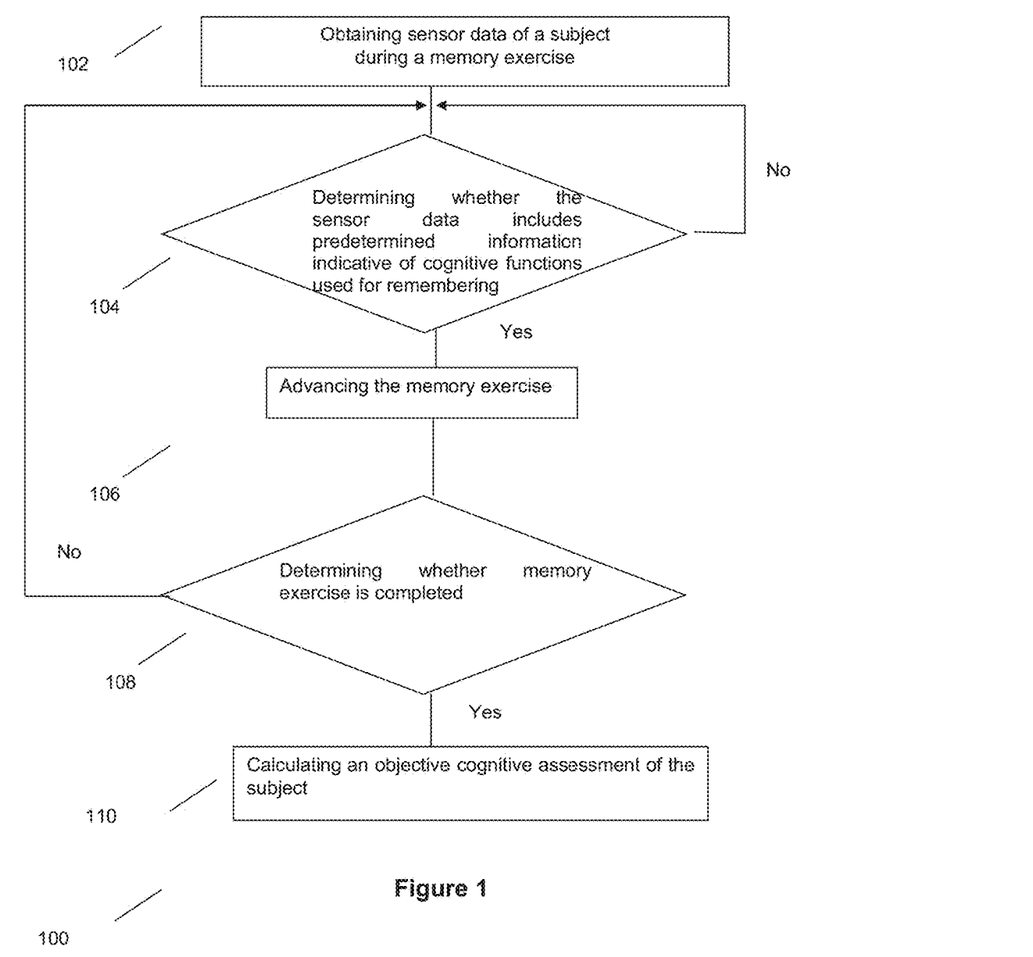
FIG. 1 shows a flowchart that illustrates a method for cognitive training according to a first embodiment.

FIG. 1 shows a flowchart 100 that illustrates a method for cognitive training according to a first embodiment. This methodology provides cognitive training for a subject in a personalized manner.

In step 102, sensor data relating to a subject is obtained. In step 104, it will be determined whether or not the sensor data includes predetermined information indicative of cognitive functions used for remembering. In an embodiment, the sensor data could come from physiological and/or behavioral sensor. In another embodiment, the sensor data could come from video camera and/or electroencephalography (EEG) electrode. In step 106, the memory exercise is advanced. In step 108, it will be determined whether or not the memory exercise is completed. In step 110, an objective cognitive assessment is calculated.

In step 104, the obtained sensor data from step 102 will be compared with predetermined information indicative of cognitive functions used for remembering to determine whether or not the sensor data includes the predetermined information. The presence of the predetermined information indicates that the subject is using cognitive functions for remembering.

When it is determined that the sensor data includes predetermined information indicative of cognitive functions used for remembering, the memory exercise will advance in step 106. In, the event that it is determined that the sensor data does not include predetermined information indicative of cognitive functions used for remembering, step 104 will be repeated until it is determined that the sensor data includes the predetermined information indicative of cognitive functions for remembering:

The determining step includes determining when a predetermined portion of the memory exercise is completed in predetermined time duration. In one instance, an indicator is provided to illustrate to the subject the progress of completing the portion of the memory exercise within the predetermined time duration. The indicator may be a visual signal, light signal or an audio signal. In the event that the portion of the memory exercise is not completed within the predetermined time duration, step 104 will be repeated and the indicator will indicate the same to the subject.

The determining step includes whether a score is achieved for a current level of the memory exercise in step 104 before the memory exercise will advance in step 106. The score is taken based on several parameters, i.e., time taken to complete the memory exercise, the complexity and difficulty of the exercise, accuracy of the subject, profile and condition of the subject. The score can be adjusted according to the requirements of the subject. The score indicates a measure of the cognitive function used for remembering when at least a portion of the memory exercise is completed.

In step 108, it is determined whether the memory exercise is completed. When it is determined that the memory exercise is completed, step 110 is invoked. The results from step 110 provide for a value that is an objective assessment of the cognitive ability for remembering of the subject, based on documented parameters suitable for the subject and the performance of the subject during the exercise, i.e., time taken to complete the exercise and the accuracy. The objective cognitive assessment obtained in step 108 can be used to adjust the predetermined information that is used in the determining step 104.

The performance of the subject for the completed memory exercise will be assessed in response of the calculated objective cognitive assessment. The subject profile will be updated accordingly in response to the objective cognitive assessment. This allows the clinical professionals to keep track of the progress of the training.

The memory exercise is then configured in response to the objective cognitive assessment of the subject and the subject profile. This provides a personalized cognitive training method for the subject in accordance to the condition and needs of the subject. The predetermined information that is used in the determining step will also be adjusted accordingly. If the subject has completed the memory exercise before the expected time duration, the predetermined duration that is used in determining whether the sensor data includes the predetermined information will be shortened and the reverse applies. If the subject were to take a longer time to complete the memory exercise than expected, the predetermined information that is used in analyzing the sensor data will be adjusted accordingly. In this manner, a personalized memory exercise will be provided.

Figure 2:
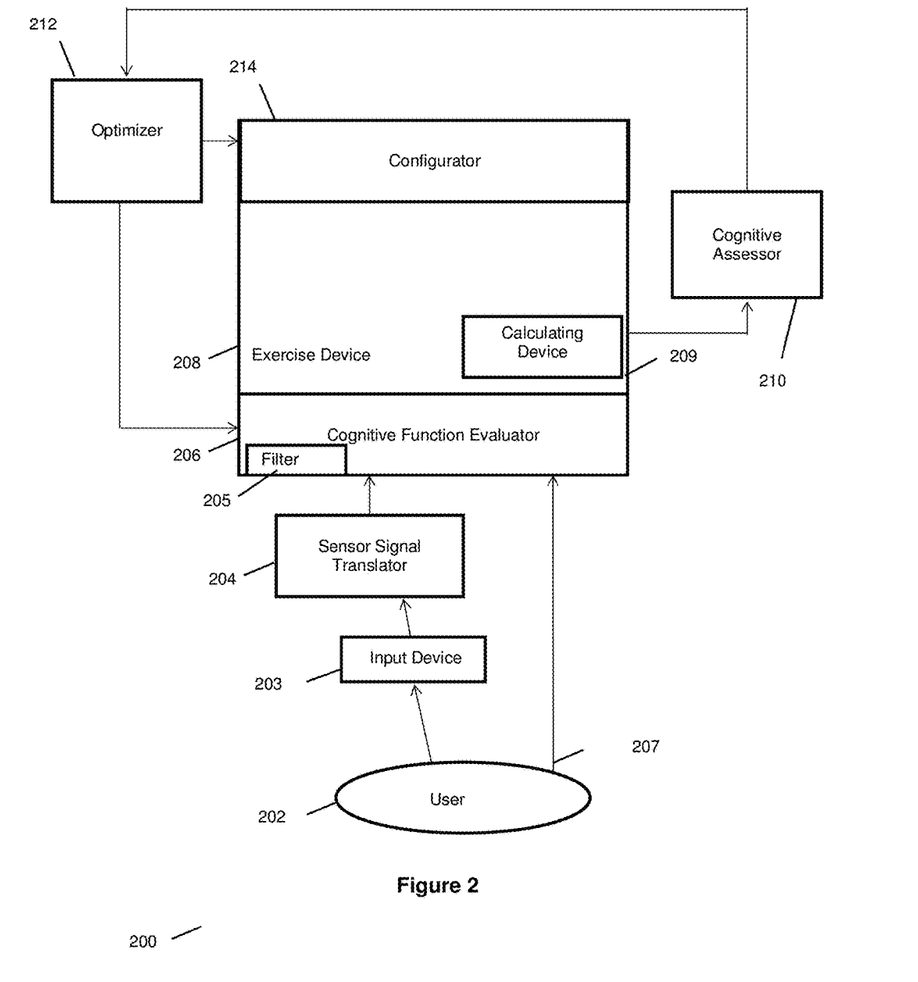
FIG. 2 shows an autodidactic cognitive training device, according to a second embodiment.
Figure 3:
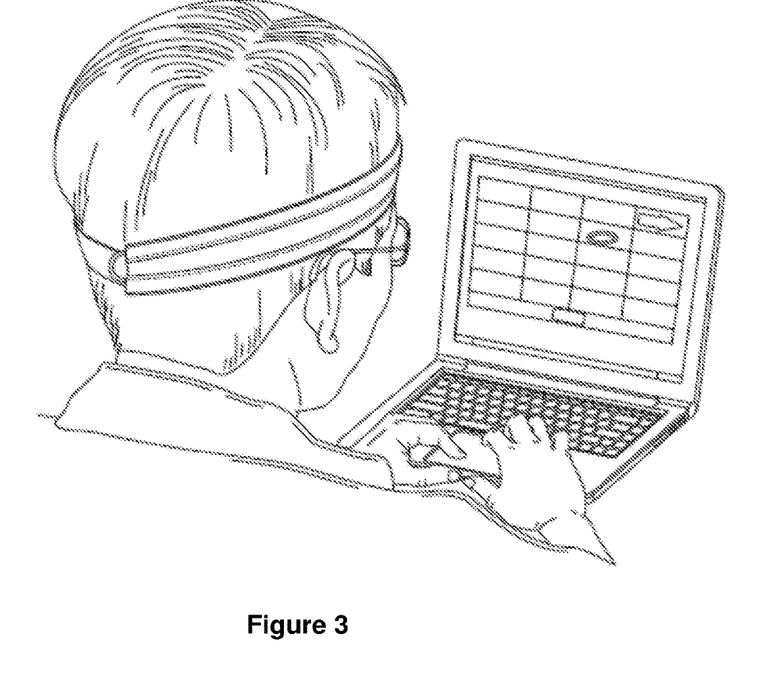
FIG. 3 shows a picture of a setup for brain computer interface training.

FIG. 2 shows an apparatus 200, according to a second embodiment for cognitive training. Sensor data is acquired via an input device 203. An example of the input device 203 is an electrode that is attached to the forehead of the subject, as illustrated in FIG. 3. In one embodiment, the input device 203 could be physiological and/or behavioral sensor. In another embodiment, the input device 203 could be a video camera and/or electroencephalography (EEG) electrode.

The input device 203 is arranged to be coupled to the cognitive function evaluator 206. The cognitive function evaluator 206 is adapted to determine whether the sensor data includes predetermined information indicative for remembering.

The cognitive function evaluator 206 is further adapted to determine when a predetermined portion of the memory exercise is completed in predetermined time duration. In one instance, an indicator is provided to illustrate to the subject the progress of completing the portion of the memory exercise within the predetermined time duration. The indicator may be a visual signal, light signal or an audio signal. In the event that the portion of the memory exercise is not completed within the predetermined time duration, the cognitive function evaluator will repeat the determining step and the indicator will indicate the same to the subject.

In an embodiment, there is a sensor signal translator 204 that is adapted to translate the acquired sensor data via input device 203 for use in the cognitive function evaluator 206 to determine whether the translated sensor data includes the predetermined information indicative of cognitive functions for remembering. In another embodiment, the sensor signal translator 204 could be an EEG translator and could be adapted to translate the acquired EEG data for use in the cognitive function evaluation 206 to determine whether the translated sensor data includes the predetermined information indicative of cognitive functions for remembering.

In an embodiment, the cognitive function evaluator 206 comprises a filter 205. The sensor data received from the input device 203 or sensor signal translator 204 will be passed through the filter 205 before the cognitive function evaluator 206 determines whether the sensor data includes the predetermined information.

The cognitive function evaluator 206 is coupled to an exercise device 208. The exercise device 208 is adapted to advance the memory exercise when it is determined that the sensor data includes the predetermined information indicative of cognitive functions used for remembering. The exercise device 208 is adapted not to advance when it is determined that the sensor data does not include the predetermined information indicative of cognitive functions used for remembering. The exercise device 208 is adapted to determine whether or not a score is achieved for a current level of the memory device and advance the memory exercise accordance with machine learning techniques when it is determined that the score is achieved for the current level of the memory exercise. The score indicates a measure of the cognitive function used for remembering when at least a portion of the memory exercise is completed.

The exercise device 208 includes a calculating device 209 that is adapted to calculate an objective cognitive assessment of the subject in accordance with probabilistic modeling when it is determined by the exercise device that the memory device is completed. In an embodiment, the calculating device 209 calculates the objective cognitive assessment of the subject in response to the performance and/or score of the subject, i.e., time taken to complete the memory exercise, accuracy of the performance.

The exercise device 208 is coupled to a cognitive assessor 210 that is adapted to receive the calculated objective cognitive assessment of the subject. The cognitive assessor 210 assesses the performance of the subject for the memory device in response to the calculated objective cognitive assessment.

The cognitive assessor 210 is coupled to an optimizer 212 which is adapted to store information including the sensor data from input device 203 and the sensor signal translator 201, parameters pertaining to the memory exercise, and a subject profile corresponding to the subject. The subject profile includes the condition and historic objective cognitive assessment from completing the memory exercises. The optimizer 212 is adapted to receive the assessed objective cognitive assessment and update the subject profile accordingly in response to the objective cognitive assessment. This allows the clinical professionals to keep track of the progress of the training.

The optimizer 212 is coupled to a configurator 214 which is adapted to configure the memory exercise in response to the assessed objective cognitive assessment of the subject and the subject profile. This provides a personalized cognitive training method for the subject in accordance to the condition and needs of the subject. In one embodiment, the configurator 214 adjusts the predetermined information that is used in the determining step by the cognitive function evaluator 206 in response to the assessed objective cognitive assessment. If the subject has completed the memory exercise before the expected time duration, the predetermined duration that is used in determining whether the sensor data includes the predetermined information will be shortened and the reverse applies. If the subject were to take a longer time to complete the memory exercise than expected, the predetermined information that is used in analyzing the sensor data will be adjusted accordingly.

In one embodiment, the configurator. 214 will configure the predetermined duration that is used in determining whether the sensor data includes the predetermined duration in response to the assessed objective assessment. If the subject has completed the memory exercise before the expected time duration, the predetermined duration that is used in determining whether the sensor data includes the predetermined information will be shortened and the reverse applies.

In one embodiment, the configurator 214 configures the complexity and/or difficulty of the memory exercise in response of the assessed objective cognitive assessment. If the subject has completed the memory exercise before the expected time duration, the complexity and for difficulty of the memory exercise will be increased and the reverse applies.

In one embodiment, the optimizer 212 is coupled to the cognitive function evaluator 206. The cognitive function evaluator 206 will configure the predetermined information indicative of cognitive functions for remembering in response to the assessed objective assessment. If the subject has completed the memory exercise before the expected time duration, the predetermined information that is used in determining step will be increased and the reverse applies.

In one embodiment, the cognitive function evaluator 206 will configure the predetermined duration that is used in determining whether the sensor data includes the predetermined duration in response to the assessed objective assessment. If the subject has completed the memory exercise before the expected time duration, the predetermined duration that is used in determining whether the sensor data includes the predetermined information will be shortened and the reverse applies.

In an embodiment, there is a second input 207 from the user via the selection made during the memory exercise. This can be in the form of keyboard, joystick or computer mouse control.

Figure 4:
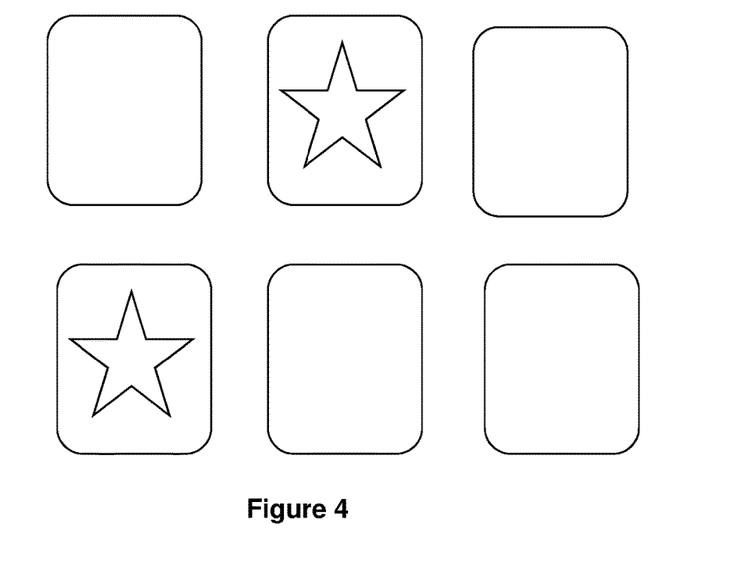
FIG. 4 shows a plan view of a memory exercise.

FIG. 4 shows that in accordance with the present embodiment, the memory exercise includes flipping and matching cards illustrating pictures and/or words in different languages. Memory of a subject includes immediate memory, visuospatial/constructional memory, attention memory and delayed memory. The actual performance of the memory of the subject is determined by the subject's speed and the difficulty of the memory exercise. One example is the time duration needed for a subject to flip and match the cards' which utilizes the subject's cognitive function. Through this memory exercise, the objective cognitive assessment measures the performance of cognitive function for remembering, i.e., memory of the subject.

However, those skilled in the art will realize that many other exercises could be used so long as they measure the performance of the memory by addressing two or more of the four components in memory including immediate memory, visuospatial/constructional memory, attention memory and delayed memory.

The memory exercise requires the sensor data acquired from the subject to meet predetermined information before the exercise will advance, hence, the subject is required to use the cognitive function for remembering so as to complete the exercise. In the event that the subject is not using the cognitive function for remembering in a manner that is suitable for him/her, the subject will be informed by the indicator.

Existing techniques may assume cognitive function and simple indicator of the difficulty like the number of cards in the memory exercise. However, varying cognitive efforts in the same subject and different level of difficulty associated with even the same number of cards will easily render such techniques inaccurate and their results inconsistent from time to time. Therefore, embodiments of the invention seek to solve the problem in the following way.

First, it incorporates image processing techniques to automatically analyse the similarity matrix between cards. It then computes a mathematical model of difficulty that combines the similarity measure and the size of the card tiles. Second, the subject's actual cognitive function for remembering is measured and used to normalize the cognitive workload using an appropriate mathematical model. A robust mathematical model is applied that combines results from multiple test sessions into an objective measurement of memory capacity, which minimizes the effects of irrelevant conditions.

Embodiments use the information from the objective cognitive assessment to probabilistically maximize the effect of training. The configurator 214 configures the difficulty measure. In an embodiment where the memory exercise involves matching of pairs of cards having the same pictures, this will be done by optimizing the number of cards and the selection of cards so as to best match the difficulty measure to the subject's cognitive capacity.

For example, the difficulty measure can be controlled such that the subject will be expected to complete it within a given time. The embodiment also adjusts the predetermined information for generating the indicator, such that the subject is able to complete tasks efficiently.

The performance index is calculated computationally. Two variables are considered, namely, the difficulty level $\lambda$ of a computer-based training game (or a computer-based memory exercise, without loss of generality, we use the term training game that also covers the memory exercise), and the minimum of the expectation of time cost $\tau$ for completing the game by the subject.

Time is also affected by the workload or the cognitive function of the subject during the memory exercise. Therefore, in one embodiment, $\tau$ is considered as the theoretical time in which the subject is fully utilizing the cognitive function for remembering.

Figure 5:
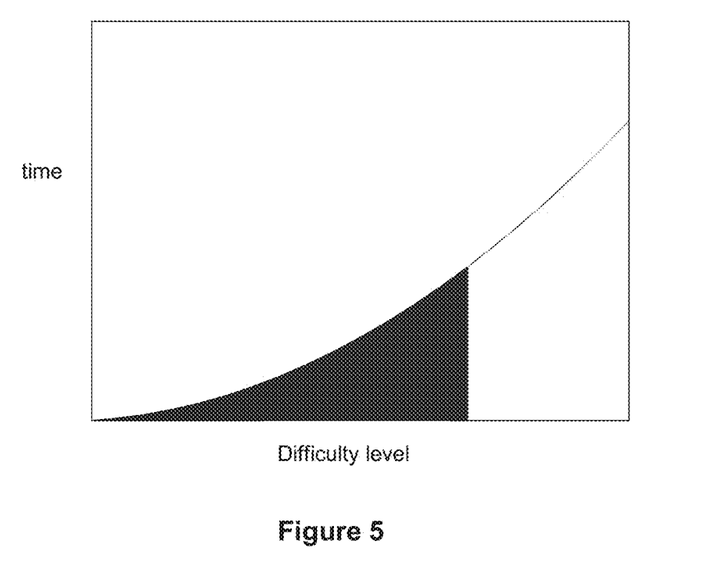
FIG. 5 shows a graphical representation of the change in difficulty level and the time taken.

FIG. 5 shows a graphical representation of the change in difficulty level and the time taken. Consider the time $\tau$ as a function of the difficulty level $\lambda$. Both variables are non-negative. To factor in various difficulty levels, the area under the function curve from 0 is used up to a specified difficulty level, $\lambda_0$ $$P=\int_0^{\lambda_0} \tau(\lambda)d\lambda \tag{1}$$

The time $\tau$ is a monotonic function over $\lambda$, since a more difficult game requires a longer time to finish. Mathematically, it says $$\frac{d\tau}{d\lambda} \geq 0, \lambda \geq 0 \tag{2}$$

A that objectively quantifies the difficulty of a game is measured in the following way. Without loss of generality, the game of remembering is used as an example. Given a layout of a game, there are a few factors that determine the difficulty.

Number of cards, which can be described by an even number n

Distance between each pair of cards, which can be described by a matrix K;

Similarity between each pair of cards, which can be described by a matrix S;

The difficulty is determined by the three variables.

$$\lambda=f(K,S,n) \tag{3}$$

It should be noted that the three variables are dependent. For example, the size of K and S are essentially determined by n×n The following model describes the function by ignoring K and reducing the information in the matrix S to the mean similarity s between pairs.

$$\lambda = \exp\left(\alpha s\left(\frac{n}{2} - 1\right)\right) - 1 \tag{4}$$

Figure 6:
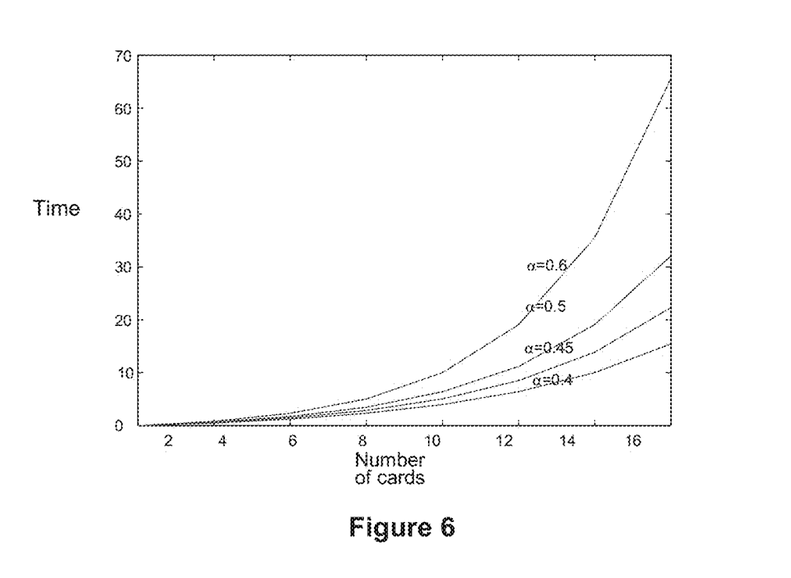
FIG. 6 shows a graphical representation of the change in number of cards and the difficulty level.

FIG. 6 shows a graphical representation of the change in number of cards and the difficulty level.

In the event that a subject plays and finishes memories exercise in time $\tau_0$, this time is determined by both the subject's cognitive function ability, as well as the difficulty of the game. With the algorithm decoding information about cognitive functions associated with remembering, the variable of cognitive function is reduced by introducing a normalized time duration in which the subject can finish the session if fully utilizing his/her cognitive function for remembering.

$$\tau = \tau_0 \left[ \int_0^\tau \left( \frac{1}{1+e^{\alpha(t)}} \right) dt \right]^{-1} \quad (5)$$

The overall memory capacity shall take into account all the possible difficulty level. However, given a number of samples of difficulty-time pairs, it is not straightforward to estimate the area under the function curves till a given upper bound of difficulty level.

Therefore, for computing the performance index as in Eq. 1, samples of time and difficulty level are computed above, except the coefficient $\alpha$ in Eq. 4 which requires determination. Estimating the function in Eq. 1 becomes a curve-fitting problem.

Since the difficulty level above already accounts for high orders, the relationship between it and the time is expected to be of a low order. Particularly, consider an M-th order polynomial estimation given by Eq. 6:

$$y = \Sigma_{j=1}^M b_j x^j \quad (6)$$

The zero-order is dropped since y=0 for x=0.

For this estimate to be monotonic in the range of [0, ∞], a strong, sufficient condition is $$b_j \geq 0 \forall j \quad (7)$$

Therefore, both the coefficients b's and $\alpha$ need to be determined. In the event that there is a data set of N samples of training game data in terms of triples: $\bar{s}_i$ (reminder: the mean similarity measure of images in the training game), $n_i$ the number of image tiles, and the normalized time duration $\tau_i$ for completing the game, it is possible to summarize the above description to formulate the function of $\tau$ with respect to the variables $$\tau_{\alpha,b}(\bar{s}, n) = \sum_{j=1}^M b_j \left[ \exp\left(\alpha \bar{s}\left(\frac{n}{2} - 1\right)\right) - 1 \right]^j \quad (8)$$

Then the optimization problem is formulated as $${}_{\alpha,b \geq 0}^{max} \Sigma_{i=0}^N (\tau_{\alpha,b}(\bar{s}_i, n_i) - \tau_i)^2 \quad (9)$$

Optimization toolboxes are then utilized to solve the problem. Since the function is highly nonlinear, a globally optimum solution may not be guaranteed.

With the estimated coefficients, the performance index, defined by the area under the curve is then given by $$P = \int_0^{x_0} \sum_{j=1}^M b_j x^j \, dx = \sum_{j=1}^M \frac{b_j}{j+1} x_0^{j+1} \quad (10)$$

Use of the area under the curve rather than use of the time at a particular difficulty level can provide a more robust estimation of performance, since the latter is more susceptible to noise and also does not account for varying difficulty levels. Besides, this allows prediction of a subject's overall performance up to an arbitrary difficulty level.

In the scenario that the subject undergoing the exercise shall complete a round of memory exercise within a given time at a maximum possible difficulty level, this can be casted as a statistical problem:

$$P(\tau \leq \tau_0 | \lambda_{pl}) \leq \zeta_c \quad (11)$$

where $t_0$ is the given time for the subject to complete the game, $\zeta_C$ is a confidence level, e.g., 0.95.

For each difficulty level, the time $\tau$ can be modelled as a non-negative function described by Eq. 8.

Using maximum entropy principle, the variable $\tau$ shall be Gamma distributed where the distribution function is determined by two parameters: the scale parameter $\theta$ (or its inverse, the rate parameter $$\lambda = \frac{1}{\theta}$$

and the shape parameter k. That is, $$p(\tau; k, \theta) = \frac{1}{\theta^k} \frac{1}{\Gamma(k)} \tau^{k-1} e^{-\frac{\tau}{\theta}}; \tau \geq 0 \text{ and } k, \theta > 0 \quad (12)$$

where $\Gamma(\ )$ is a gamma function given by $$\Gamma(k) = \int_0^\infty t^{k-1} e^{-t} dt \quad (13)$$

Since each difficulty level is associated with a particular random variable for the time $\tau$, the two parameters k and $\theta$ are essentially functions of the difficulty level. Practically, we may choose an appropriate k to match the shape of the empirical distribution and then $\theta$ is easily determined by both mean and k since $\bar{\tau} = k\theta$.

The cumulative distribution function (CDF) of the gamma function is then $$F(\tau; k, \theta) = \frac{1}{\Gamma(k)} \gamma \frac{\tau}{\theta} \quad (14)$$

where $\gamma(\ )$ is the incomplete gamma function.

Then the selection of difficulty level is by solving the following problem $$\max \lambda(n, \bar{s}) \text{ subject to } F(t_0; k(\lambda), \theta(\lambda)) \leq \zeta_C \quad (15)$$

In a practical system with a finite number of image subsets, every subset and the difficulty level using n and $\bar{s}$ are computed. Then CDFs and the largest one with CDF no larger than $\zeta_C$ are calculated.

The device and method employ a personalized approach that aims to maximize the training efficiency for each subject. Particularly, this is obtained by using an automated mechanism, called personalized training configuration optimization (PTCO). This mechanism determines the layout of the training program and sets the parameters that best fit to the subject's conditions in terms of behavioral condition and cognitive condition. The two conditions will be evaluated using the other two unique components: the sensor signal translator using the brain-computer interface technology, and the cognitive assessment engine.

The basic scientific principle is that interactions between attention and working memory have been established in neuroscience and psychology. Yet, combining the two through active neuro-physiological computing for more effective cognitive training is a new area, and the feasibility and effects needs to be validated both technically and clinically.

The core technology comprises the following.

A computer-based system for simultaneous training of memory and attention that uses advanced neurocomputing and machine learning techniques;

An objective cognitive (memory) assessment tool that provides information for optimizing training program as well as for cognitive evaluation in clinical use;

An automatic, personalized setting optimization method with probabilistic modelling of difficulty level;

Incorporation of advanced attention detection method that uses physiologic data to evaluate the attention condition in real-time;

New system comprising server-based training system supporting multiple clients

Figure 7:
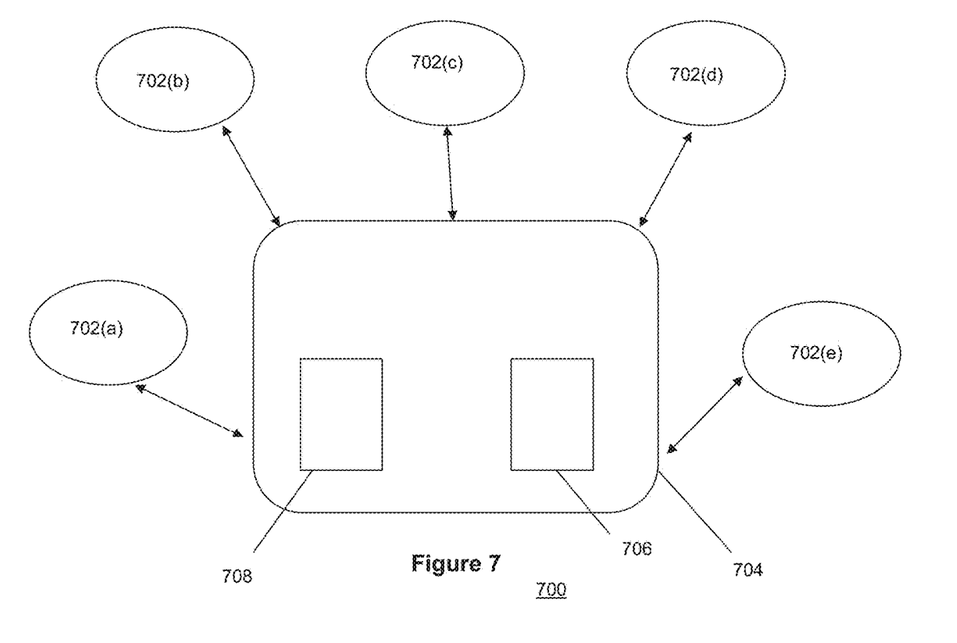
FIG. 7 shows a block diagram of autodidactic cognitive training devices in a system.

FIG. 7 shows a block diagram of the devices 702 (a)-(e) in a system 700. In accordance with the present embodiment, the system 700 has at least one of the devices 702(a)-(e) and a server 704 including a receiver 706. The receiver 706 is operable to receive the objective cognitive assessment of the subject from the at least one of the devices 702(a)-(e). The system 700 also includes a data storage 708 for receiving and storing the subject profile from the at least one of the devices. The system 700 is also operable to correlate two or more subjects with their respective objective cognitive assessment when it is coupled to two or more of the devices 702 (a)-(e).

A fifth embodiment provided a computer readable medium for cognitive training. The computer readable medium has stored thereon computer program code which when executed by a computer causes the computer to perform at least the following: obtaining sensor data of a subject during a memory exercise; determining whether the sensor data includes predetermined information indicative of cognitive functions used for remembering; advancing the memory exercise when it is determined that the sensor data includes predetermined information indicative of cognitive functions used for remembering; and calculating an objective cognitive assessment of the subject in response to completion of the memory exercise; wherein cognitive training is measured at least partially in response to the advancing the memory exercise.

Experiments and Discussion

Participants

A total of 38 subjects were assessed for eligibility, among which 3 were excluded for not meeting the criteria. A total of 35 participants were randomized (17 in brain-computer interface (BCI) intervention and 18 in waitlist control). Two participants were found to be ineligible and had been incorrectly randomized; neither received any of the intervention. This left a total of 33 patients in the intention-to-treat (ITT) population, 15 in BCI intervention and 18 in waitlist control. One participant was lost to follow-up after randomization and one other withdrew after completing the week one assessment (both from the waitlist control arm). Neither received any intervention. Therefore, of these 33 in the ITT population, 31 (15 in BCI intervention and 16 in waitlist control) contributed information to the primary efficacy and acceptability analysis. All 31 participants completed all 24 sessions (adherence rate: 100%).

Procedure

The BCI system used in the present study has been elaborated upon in a previous publication. Before training, all participants underwent a calibration Stroop task. This Stroop task allowed the BCI system to develop an individualized EEG profile representing each participant's attentive state.

Participants in both the intervention and the wait-list group underwent the BCI intervention for 24 sessions over the span of 8 weeks. Each session was planned to take 30-minutes to complete. During each session, participants played a card-pairing memory game, in which they had to focus their attention in order to open or close the cards on screen (see FIG. 3). After each training session, participants were queried as to whether they experienced any adverse events. The intervention group underwent the BCI treatment in their first 8 weeks of being in the trial. The waitlist control arm did not undergo the intervention until after 8 weeks. From Week 9 to 16 the waitlist control arm underwent the same BCI training intervention procedure as the Intervention Arm. All study procedures from the first recruitment to the last follow up was completed between April 2012 and January 2013.

Outcome Measures

A usability and acceptability questionnaire was administered at each participant's final BCI training session (week 8 for intervention arm and week 16 for the waitlist control). Participants rated how strongly they agreed with each item on a scale of 1 (Strongly Disagree) to 7 (Strongly Agree).

TABLE 1

Descriptive summary of responses to all items in the usability and acceptability questionnaire

| Questionnaire item | Mean | SD | Median | Range |
|---|---|---|---|---|
| Overall I am satisfied with how easy it is to use this device. | 6.4 | 0.8 | 7 | 4 to 7 |
| I feel comfortable using this device. | 6.4 | 0.7 | 6 | 5 to 7 |
| I enjoyed playing the game. | 6.8 | 0.5 | 7 | 5 to 7 |
| I think the device is useful in training my memory and attention. | 6.6 | 0.8 | 7 | 4 to 7 |
| I will recommend this device to my friends and family. | 6.5 | 0.8 | 7 | 4 to 7 |
| Overall I am satisfied with the interface of the game. | 6.5 | 0.6 | 7 | 5 to 7 |
| Overall I am satisfied with the whole system. | 6.5 | 0.7 | 7 | 1 to 7 |

The efficacy outcome measure was the total score of Repeatable Battery for the Assessment of Neuropsychological Status (RBANS), which was conducted for the intervention arm at Weeks 1, 8 and 16; and the waitlist control arm at Weeks 1, 9 and 16. Adverse or serious adverse events were assessed by querying participants after each session of BCI training if they have experienced any discomfort during the session. A summary of these events, if any, were then collated for each participant at the end of the study.

The primary endpoints were: acceptability rate of the BCI device based on participants overall rating scores on a usability questionnaire; and change in total score of the RBANS at week 8 from week 1. Acceptability rate was defined as proportion of participants whose rating score to the whole system was greater than 4 (scale range 1-7).

Secondary endpoints included: adherence rate which was defined as the proportion of participants who finished no fewer than 19 BCI sessions (out of 24 offered); changes in the five domain scores of the Repeatable Battery for the Assessment of Neuropsychological Status (RBANS) at week 8 from week 1, and the change between pre and post BCI sessions for the five domain scores of the RBANS and the total scale index score pooled across groups.

Changes in RBANS Scores

The median scores of the two arms in the two periods are shown in Table 3. The median difference in the RBANS total scale index score between week 8 and week 1 in the intervention arm pre and post training was 3.0 (range −6 to 28), as shown in Table 2. In the waitlist control arm, the corresponding median of the difference was 2.0 (−18 to 19) during the waitlist period. The waitlist control arm received the BCI intervention between week 9 and 16. The median of the difference in the RBANS total scale index score was 4.5 (−9 to 22) during the intervention period. The corresponding median of the difference between week 8 and week 16 in intervention arm who did not receive treatment during this period was 1.0 (−20 to 29).

The Hodges-Lehmann estimate of the median difference in the change scores (from week 1 to week 8) of the total RBANS score between arms was 7.0 (95% CI: −4.0 to 15.0; p=0.332) which was not statistically significant. The point estimate (7.0) reflects an effect size of approximately 0.6 SD. The Hodges-Lehmann estimate of the median differences between arms in the change scores (from week 1 to week 8) of the 5 RBANS domains ranged from 0.5 to 9.5, suggesting an improvement in each of the domains for those participants in the intervention arm. However, none of the differences in change scores across the domain scores were statistically significantly different (Table 2).

Pooling the pre and post BCI data from both arms, the median of the changes in total score of the RBANS pre and post BCI was 4.0 (95% CI: −9.0 to 28.0; p<0.001) (Table 3). The median of the changes in immediate memory, visuospatial/constructional, attention and delayed memory domain scores pre and post BCI, both arms pooled, were all statistically significant, except the language domain score.

TABLE 3

Changes of RBANS individual index sub-scores and total scale index score pre and post intervention, pooling data from both Intervention and Waitlist control arms.

| Change in RBANS scores pre and post-treatment | Summary statistics | P-value[1] |
|---|---|---|
| RBANS Domain Index Scores | | |
| Immediate Memory | | |
| Mean (SD) | 6.9 (17.6) | |
| Median (range) | 6.0 (−28 to 44) | 0.038 |
| Visuospatial/Constructional | | |
| Mean (SD) | 5.2 (11.2) | |
| Median (range) | 4.0 (−13 to 32) | 0.014 |
| Language | | |
| Mean (SD) | 2.4 (16.8) | |
| Median (range) | 0.0 (−30 to 42) | 0.547 |
| Attention | | |
| Mean (SD) | 3.4 (11.0) | |
| Median (range) | 6.0 (−27 to 25) | 0.039 |
| Delayed Memory | | |
| Mean (SD) | 6.1 (10.0) | |
| Median (range) | 6.0 (−12 to 37) | <0.001 |

[1]P-value from the Wilcoxon signed rank test

Safety

There were no adverse or serious adverse events reported during the study period by any of the participants.

Discussion

As seen from the responses for the usability and acceptability questionnaire, feedback from participants was positive. The very high adherence rate also suggested a high

TABLE 2

A comparison of change in RBANS Domain Index Scores between Week 1 and Week 8 for Intervention and Waitlist control arms

| Change in RBANS Scores between Week 1 and 8 | Intervention | Wait-list | P-value[1] | Median diff. (95% CI)[2] |
|---|---|---|---|---|
| Immediate Memory | | | | |
| Mean (SD) | 8.3 (18.4) | −1.8 (17.2) | | |
| Median (range) | 6.0 (−17 to 44) | −3.0 (−33 to 40) | 0.160 | 9.5 (−3.0, 25.0) |
| Visuospatial/Constructional | | | | |
| Mean (SD) | 4.1 (12.3) | 3.5 (15.4) | | |
| Median (range) | 4.0 (−13 to 32) | 1.5 (−21 to 37) | 0.782 | 2 (−10.0, 12.0) |
| Language | | | | |
| Mean (SD) | 0.1 (21.6) | −1.4 (20.7) | | |
| Median (range) | −4.0 (−30 to 42) | 0.0 (−36 to 38) | 0.937 | 0.5 (−15.0, 17.0) |
| Attention | | | | |
| Mean (SD) | 4.1 (12.2) | 3.0 (13.5) | | |
| Median (range) | 6.0 (−27 to 25) | 1.5 (−29 to 31) | 0.677 | 1 (−6.0, 10.0) |
| Delayed Memory | | | | |
| Mean (SD) | 6.5 (11.2) | 2.1 (11.3) | | |
| Median (range) | 4.0 (−7 to 37) | 0.0 (−24 to 22) | 0.362 | 2.5 (−4.0, 11.0) |
| RBANS Total Scale Index Score | | | | |
| Mean (SD) | 7.6 (11.4) | 1.2 (11.3) | | |
| Median (range) | 3.00 (−6 to 28) | 2.0 (−18 to 19) | 0.332 | 7 (−4.0, 15.0) |

[1]P-value from the Mann-Whitney U test
[2]Hodges-Lehmann estimation and its associated 95% confidence interval level of motivation among the participants. These factors indicated that elderly users may be sufficiently motivated to adhere to the training program even in their own homes.

RBANS total scores improved by a similar magnitude pre and post training, and this occurred for both intervention and waitlist control arms (between Week 1 and 8 for intervention, and Week 9 and 16 for waitlist control). The RBANS total scores did not change in the waitlist control arm before the intervention. In addition, between Weeks 9 and 16 when the intervention arm ceased treatment, their mean RBANS total score neither decreased to baseline level nor improved at an equally large magnitude as between weeks 1 and 8. The time sequence of the changes can be taken as support that improvements in mean RBANS total scores between weeks 1 and 8 for the intervention arm were due to the BCI treatment effect.

While the data indicated that the intervention arm showed a larger improvement in RBANS total scores between Weeks 1 and 8 as compared to the waitlist control arm, this difference did not reach statistical significance. Thus, the study does not provide conclusive evidence for a difference in attention and memory in the normal elderly as assessed by the total score on the RBANS between intervention arm and waitlist control. Nevertheless, an effect size of 0.6 SD was obtained. This decision is also supported by the highly significant result obtained when data from both arms were pooled, showing a positive shift in RBANS total scores pre and post-BCI training.

It is notable that, pooling both arms, the scores for all five RBANS domains showed statistically significant positive changes pre and post BCI, except for language. This differentiated improvement suggests that gains in RBANS scores are valid indications of the efficacy of the training program, which targets attention and memory but not language. The significantly positive change in Visuospatial/Constructional could be attributed to the visual and pictorial nature of the memory task. This may have honed the participants' attentiveness to pictorial stimuli, which are used to assess the Visuospatial/Constructional domain in RBANS. In addition, while the nature and modality of tasks used in training and assessment were very different (e.g. visual memory of pictures vs auditory memory of word lists), putative improvements in memory and attention during training were translated to score increases in both the relevant domain and global scores for RBANS. This could be taken as further evidence that the training results in global rather than task-specific improvements in cognitive functioning.

While several exemplary embodiments have been presented in the foregoing detailed description of the invention, it should be appreciated that a vast number of variations exist, including variations as to the information that is used as input and how the memory exercise is carried out.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

What is claimed is:

1. An autodidactic method for personalized memory training, comprising:
   coupling one or more electroencephalography (EEG) electrodes to a subject;
   obtaining real-time sensor data of a subject during a memory exercise, the real-time sensor data comprising EEG data obtained from the subject by the one or more EEG electrodes during the memory exercise and visual data of the subject obtained from a video camera viewing the subject during the memory exercise;
   determining throughout the memory exercise whether the real-time sensor data includes predetermined information indicative of cognitive functions used for remembering, wherein a subject's cognitive functions used for remembering comprise immediate memory, visuospatial memory, attention memory and delayed memory, and wherein the memory exercise is configured to evaluate in real-time at least two of the subject's cognitive functions used for remembering as the subject performs the memory exercise;
   advancing the memory exercise when it is determined that the real-time sensor data includes the predetermined information indicative of the cognitive functions used for remembering;
   calculating an objective cognitive assessment of the subject for determining memory functions of the subject in response to completion of the memory exercise within a predetermined time duration, the objective cognitive assessment of the subject measuring the subject's performance of the cognitive functions used for remembering as such performance varies throughout the memory exercise and calculated in response to the advancing of the memory exercise, time taken to complete the memory exercise and accuracy of the subject's performance of the memory exercise; and
   revising the memory exercise to test for an adjusted set of the subject's cognitive functions used for remembering in response to the calculated objective cognitive assessment of the subject by reconfiguring the predetermined time duration for completion of the memory exercise and a complexity of the memory exercise in response to the objective cognitive assessment of the subject.

2. The method according to claim 1, wherein the memory exercise will not advance when it is determined that the real-time sensor data does not include the predetermined information indicative of the cognitive functions used for remembering.

3. The method according to claim 1, wherein determining whether the real-time sensor data includes the predetermined information indicative of the cognitive functions used for remembering comprises determining the real-time sensor data includes the predetermined information indicative of cognitive functions used for remembering in response to one or more of a predetermined portion of the memory exercise is completed in a predetermined time duration, a complexity of the memory exercise, a difficulty of the memory exercise, accuracy of the subject and condition of the subject.

4. The method according to claim 1, further comprising determining whether a score is achieved for a current level of the memory exercise before the step of advancing the memory exercise when it is determined that the real-time sensor data includes the predetermined information indicative of the cognitive functions used for remembering, the score being indicative of the accuracy of the subject's performance of the memory exercise and time taken to complete the memory exercise, and wherein advancing the memory exercise comprises advancing the memory exercise when it is determined that the real-time sensor data includes the predetermined information indicative of the cognitive functions used for remembering and the score determined in response to the accuracy of the subject's performance of the memory exercise is equal to or greater than the score to be achieved for the current level of the memory exercise.

5. The method according to claim 1, wherein the memory exercise comprises flipping and matching cards illustrating pictures and/or words in different languages to match the pictures and/or words.

6. The method according to claim 1, wherein the step of determining whether the real-time sensor data includes the predetermined information indicative of the cognitive functions used for remembering comprises passing the EEG data through a filter to determine whether the real-time sensor data includes the predetermined information indicative of the cognitive functions used for remembering.

7. An autodidactic personalized memory training device comprising:
   at least a first input device and a second input device for receiving real-time sensor data of a subject during a memory exercise, the first input device comprising an electroencephalography (EEG) electrode for receiving real-time EEG sensor data from the subject during the memory exercise and the second input device comprising a video camera for receiving real-time visual information of the subject during the memory exercise, the real-time sensor data comprising the real-time EEG sensor data and the real-time visual information;
   a cognitive function evaluator adapted to receive the real-time sensor data from the at least the first input device and the second input device and determine whether the real-time sensor data includes predetermined information indicative of cognitive functions used for remembering, wherein a subject's cognitive functions used for remembering comprise immediate memory, visuospatial memory, attention memory and delayed memory, and wherein the memory exercise is configured for the cognitive function evaluator to evaluate in real-time at least two of the subject's cognitive functions used for remembering as the subject performs the memory exercise;
   an exercise device adapted to advance the memory exercise when it is determined that the real-time sensor data includes the predetermined information indicative of cognitive functions used for remembering, the exercise device comprising a calculating device adapted to calculate an objective cognitive assessment of the subject for determining memory functions of the subject in response to completion of the memory exercise within a predetermined time duration, the objective cognitive assessment of the subject measuring the subject's performance of the cognitive functions used for remembering as such performance varies during the memory exercise, wherein the calculating device is further adapted to calculate the objective cognitive assessment of the subject in response to the advancing of the memory exercise, time taken to complete the memory exercise and accuracy of the subject's performance of the memory exercise;
   a cognitive assessor coupled to the exercise device and operable to receive and assess the calculated objective cognitive assessment of the subject;
   an optimizer coupled to the cognitive assessor and adapted to store information, the information comprising the real-time sensor data and one or more parameters pertaining to the memory exercise; and
   a configurator coupled to the optimizer, the configurator adapted to configure the predetermined time duration for completion of the memory exercise and a complexity of the memory exercise in response to the received assessed objective cognitive assessment of the subject, the configurator revising the memory exercise to test for an adjusted set of the subject's cognitive functions used for remembering in response to the calculated objective cognitive assessment of the subject,
   wherein the cognitive assessor is adapted to transmit the assessed objective cognitive assessment of the subject to the optimizer.

8. The autodidactic personalized memory training device according to claim 7, wherein the exercise device is adapted not to advance the memory exercise when it is determined that the real-time sensor data does not include the predetermined information indicative of the cognitive functions used for remembering.

9. The autodidactic personalized memory training device according to claim 7, wherein the cognitive function evaluator is further adapted to determine the real-time sensor data includes the predetermined information indicative of the cognitive functions used for remembering in response to one or more of a predetermined portion of the memory exercise is completed in the predetermined time duration, the complexity of the memory exercise, the accuracy of the subject's performance of the memory exercise and a condition of the subject.

10. The autodidactic personalized memory training device according to claim 7, wherein the exercise device is further adapted to determine whether a score is achieved for a current level of the memory exercise in response to the accuracy of the subject's performance of the memory exercise and advance the memory exercise when it is determined that the accuracy of the subject's performance of the memory exercise is equal to or greater than the score to be achieved for the current level of the memory exercise.

11. The autodidactic personalized memory training device according to claim 7, wherein the at least the first input device and the second input device is coupled to a sensor signal translator, the sensor signal translator operable to translate the real-time sensor data received from the at least the first input device and the second input device, and wherein the cognitive function evaluator is coupled to the sensor signal translator and operable to receive the translated real-time sensor data and determine whether the translated real-time sensor data includes the predetermined information indicative of the cognitive functions used for remembering.

12. The autodidactic personalized memory training device according to claim 7, wherein the information stored in the optimizer further comprises a subject profile corresponding to the subject.

13. The autodidactic personalized memory training device according to claim 12, wherein the optimizer is further adapted to update the subject profile of the subject in response to the assessed objective cognitive assessment.

14. The autodidactic personalized memory training device according to claim 13, wherein the configurator is further adapted to configure the memory exercise in response to the updated subject profile.

15. The autodidactic personalized memory training device according to claim 14, wherein the configurator is further adapted to adjust the predetermined information indicative of the cognitive functions used for remembering corresponding to the subject in response to the updated subject profile.

16. The autodidactic personalized memory training device according to claim 7, wherein the memory exercise comprises flipping and matching cards illustrating pictures and/or words in different languages to match the pictures and/or words.

17. The autodidactic personalized memory training device according to claim 7, wherein the cognitive function evaluator comprises a filter, and wherein the cognitive function evaluator is further adapted to pass the EEG sensor data through the filter so as to determine whether the EEG sensor data includes the predetermined information indicative of the cognitive functions used for remembering.

18. The autodidactic personalized memory training device according to claim 7, wherein the exercise device is further adapted to advance the memory exercise in accordance with machine learning techniques.

19. The autodidactic personalized memory training device according to claim 7, wherein the calculating device is further adapted to calculate the objective cognitive assessment of the subject in accordance with probabilistic modeling.

20. A system for memory training comprising:
an autodidactic personalized memory training device comprising:
at least a first input device and a second input device for receiving real-time sensor data of a subject during a memory exercise, the first input device comprising an electroencephalography (EEG) electrode for receiving real-time EEG sensor data from the subject during the memory exercise and the second input device comprising a video camera for receiving real-time visual information of the subject during the memory exercise, the real-time sensor data comprising the real-time EEG sensor data and the real-time visual information;
a cognitive function evaluator adapted to receive the real-time sensor data from the at least the first input device and the second input device and determine whether the real-time sensor data includes predetermined information indicative of cognitive functions used for remembering, wherein a subject's cognitive functions used for remembering comprise immediate memory, visuospatial memory, attention memory and delayed memory, and wherein the memory exercise is configured for the cognitive function evaluator to evaluate in real-time at least two of the subject's cognitive functions used for remembering as the subject performs the memory exercise;
an exercise device adapted to advance the memory exercise when it is determined that the real-time sensor data includes the predetermined information indicative of cognitive functions used for remembering, the exercise device comprising a calculating device adapted to calculate an objective cognitive assessment of the subject for determining memory functions of the subject in response to completion of the memory exercise within a predetermined time duration, the objective cognitive assessment of the subject measuring the subject's performance of the cognitive functions used for remembering as such performance varies during the memory exercise, wherein the calculating device is further adapted to calculate the objective cognitive assessment of the subject in response to the advancing of the memory exercise, time taken to complete the memory exercise and accuracy of the subject's performance of the memory exercise;
a cognitive assessor coupled to the exercise device and operable to receive and assess the calculated objective cognitive assessment of the subject;
an optimizer coupled to the cognitive assessor and adapted to store information, the information comprising the real-time sensor data and one or more parameters pertaining to the memory exercise; and
a configurator coupled to the optimizer, the configurator adapted to configure the predetermined time duration for completion of the memory exercise and a complexity of the memory exercise in response to the received assessed objective cognitive assessment of the subject, the configurator revising the memory exercise to test for an adjusted set of the subject's cognitive functions used for remembering in response to the calculated objective cognitive assessment of the subject,
wherein the cognitive assessor is adapted to transmit the assessed objective cognitive assessment of the subject to the optimizer; and
a server coupled to the autodidactic personalized memory training device and comprising a receiver operable to receive the objective cognitive assessment of the subject from the autodidactic personalized memory training device.

21. The system according to claim 20, wherein the server is operable to receive and store a subject profile corresponding to the subject, and wherein the optimizer is further adapted to update the subject profile of the subject in response to the assessed objective cognitive assessment, and wherein the configurator is further adapted to configure the memory exercise and adjust the predetermined information indicative of cognitive functions used for remembering corresponding to the subject in response to one or more of the subject profile or the updated subject profile.

22. The system according to claim 20 further comprising two or more additional autodidactic personalized memory training devices, wherein the receiver is further operable to receive the objective cognitive assessment of two or more additional subjects calculated by the two or more additional autodidactic personalized memory training devices and wherein the server is further operable to correlate the two or more additional subjects with their respective objective cognitive assessments.

23. The system according to claim 22, wherein the server is operable to receive and store subject profiles corresponding to each of the two or more additional subjects.

24. A non-transitory computer readable medium for autodidactic personalized memory training, the computer readable medium having stored thereon computer program code which when executed by a computer causes the computer to perform at least the following:
receiving real-time sensor data of a subject during a memory exercise, the real-time sensor data comprising electroencephalography (EEG) data from one or more EEG electrodes coupled to the subject during the memory exercise and visual data of the subject obtained from a video camera viewing the subject during the memory exercise;
determining throughout the memory exercise whether the real-time sensor data obtained from the subject during the memory exercise includes predetermined information indicative of cognitive functions used for remembering, and wherein a subject's cognitive functions used for remembering comprises immediate memory, visuospatial memory, attention memory and delayed memory, and wherein the memory exercise is configured to evaluate in real-time at least two of the subject's cognitive functions used for remembering as the subject performs the memory exercise;
advancing the memory exercise when it is determined that the real-time sensor data includes predetermined information indicative of the cognitive functions used for remembering;
calculating an objective cognitive assessment of the subject for determining memory functions of the subject in response to completion of the memory exercise within a predetermined time duration, wherein the objective cognitive assessment of the subject measures the subject's performance of the cognitive functions used for remembering as such performance varies throughout the memory exercise and calculated in response to the advancing of the memory exercise, time taken to complete the memory exercise and accuracy of the subject's performance of the memory exercise; and revising the memory exercise to test for an adjusted set of the subject's cognitive functions used for remembering in response to the calculated objective cognitive assessment of the subject by reconfiguring the predetermined time duration for completion of the memory exercise and a complexity of the memory exercise in response to the objective cognitive assessment of the subject.

25. The autodidactic personalized memory training device according to claim 16, further comprising a memory exercise input control device coupled to the exercise device for the subject to flip and match the cards, the memory exercise input control device comprising one or more of a computer keyboard, a computer joy stick and a computer mouse control.

* * * * *